(12) United States Patent
Brand et al.

(10) Patent No.: US 6,934,588 B1
(45) Date of Patent: Aug. 23, 2005

(54) PACEMAKER HOUSING WITH LEAD CONNECTION ASSEMBLY

(75) Inventors: Paul Brand, Järfalla (SE); Rolf Hill, Järfalla (SE)

(73) Assignee: St. Jude Medical AB, Jarfalla (SE)

( * ) Notice: Subject to any disclaimer, the term of this patent is extended or adjusted under 35 U.S.C. 154(b) by 0 days.

(21) Appl. No.: 09/763,387

(22) PCT Filed: Aug. 17, 1999

(86) PCT No.: PCT/SE99/01383

§ 371 (c)(1),
(2), (4) Date: Apr. 18, 2001

(87) PCT Pub. No.: WO00/12174

PCT Pub. Date: Mar. 9, 2000

(30) Foreign Application Priority Data

Aug. 31, 1998 (SE) .............................................. 9802928

(51) Int. Cl.[7] .................................................. A61N 1/08
(52) U.S. Cl. ........................................................ 607/37
(58) Field of Search .............................. 607/36, 37, 38

(56) References Cited

U.S. PATENT DOCUMENTS

| | | | |
|---|---|---|---|
| 4,262,982 A | 4/1981 | Kenny | |
| 4,278,093 A | 7/1981 | Lafortune et al. | |
| 4,784,141 A | * 11/1988 | Peers-Trevarton | ...... 128/419 P |
| 4,913,147 A | 4/1990 | Fahlstrom et al. | |
| 4,934,366 A | * 6/1990 | Truex et al. | ............. 128/419 P |
| 4,991,582 A | * 2/1991 | Byers et al. | ............. 128/419 P |
| 5,324,311 A | 6/1994 | Acken | |
| 5,383,913 A | * 1/1995 | Schiff | .......................... 607/38 |
| 5,545,188 A | 8/1996 | Bradshaw et al. | |
| 5,843,141 A | 12/1998 | Bischoff et al. | |
| 6,029,089 A | * 2/2000 | Hawkins et al. | ............... 607/37 |
| 6,327,502 B1 | * 12/2001 | Johansson et al. | ............ 607/36 |

* cited by examiner

*Primary Examiner*—Jeffrey R. Jastrzab
*Assistant Examiner*—Frances P. Oropeza
(74) *Attorney, Agent, or Firm*—Schiff Hardin, LLP

(57) ABSTRACT

A pacemaker has a metallic housing with a connector arrangement adapted to receive a contact plug, with contact surfaces, at the proximal end of an electrode lead. The connector arrangement includes a metallic tubular member with opposite ends which are welded or bonded to respective openings in the metallic housing. The metallic tubular member is substantially continuous along its length between the opposite ends. All components which are needed for making electrical contact with the contact surfaces of the lead are contained within the interior of the metallic tubular member.

11 Claims, 2 Drawing Sheets

PACEMAKER HOUSING WITH LEAD CONNECTION ASSEMBLY

BACKGROUND OF THE INVENTION

1. Field of the Invention

The present invention relates to pacer housings and more particularly to those parts of the housing intended for connection to the electrode leads.

2. Description of the Prior Art

Implantable pacers normally have a pacer housing (also called can) containing electronic circuitry and a unit for electric power as well as different electrodes which are connected to the interior parts in the pacer housing and which are to be implanted in or in the vicinity of the heart. The electrodes are connected to the pacer by means of leads. The internal parts of the pacers have to be well protected against the internal environment, especially the body fluids in the body for a long period of time, which places strict requirements on all entries into the interior of the can and especially on the connections of the leads to the housing. At the same time it should be possible to disconnect the pacer from the implanted leads for replacement or servicing of the pacer. The connective parts of the pacer and the leads have largely been standardized so as to encompass a relatively deep female socket having a number of contact surfaces whereas the leads are provided with a male part comprising one or several corresponding peripheral, generally circular contact surfaces.

At present the connective part of the pacer housing containing the female socket is made of a transparent material, normally of epoxy resin, which is molded onto the housing and onto contacts extending outwardly from the housing. The male part of the leads is normally locked by means of set screws, although other fastening means have been suggested. The positioning and alignment of the different contact surfaces and of the fastening means or metallic threads for the set screws prior to the molding of the connective part is, however, complicated and the delay in the manufacturing process incurred by the curing of the epoxy resin is considerable.

It would thus be desirable if the molding procedure could be dispensed with.

It has been discussed that these complexities could be avoided by designing the pacer with a socket located inside the metal housing. This kind of sockets, sometimes termed "black holes", are not used at present.

U.S. Pat. No. 4,934,366 and U.S. Pat. No. 5,324,311, both of which are incorporated by reference, describe two interior sockets or black holes for pacers. Both designs employ a tubular member formed by a number of longitudinally alternating sections respectively made of metal and insulating ceramics. An end section of metal can be welded or bonded to an opening in the pacer housing by means of a flange. The use of different materials, however, sets high standards in regard to precision and durability of the components as well as in the assembly procedure thereof. This is especially important since the interior sockets must meet very high standards regarding the integrity of the interior of the pacer housing during long times of implantation in a demanding environment. The manufacture of these known sockets thus is relatively complicated.

SUMMARY OF THE INVENTION

An object of the invention is to avoid the aforementioned molding procedure and to simplify the design of an interior socket of a pacer connector while still meeting the required high standards for a pacer housing.

DESCRIPTION OF THE DRAWINGS

FIGS. 3–6 show a preferred embodiment of the connective part in accordance with the present invention.

DESCRIPTION OF THE PREFERRED EMBODIMENTS

Figure 1:
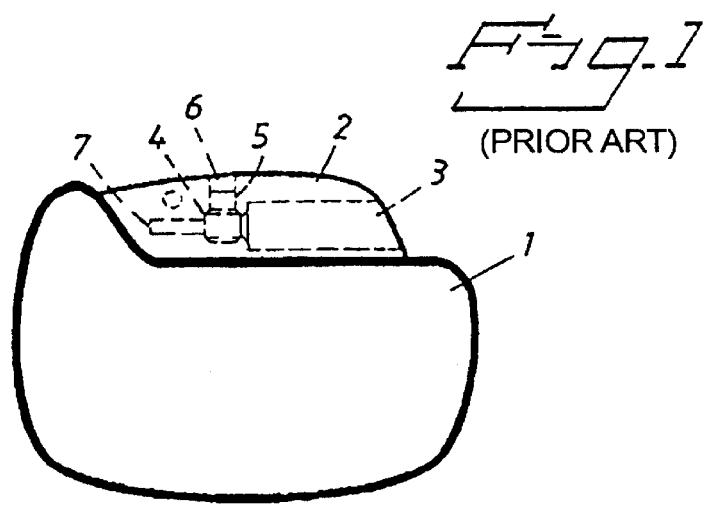
FIG. 1 shows a conventional pacer housing with a transparent, molded connective part.

FIG. 1 illustrates a conventional pacer housing 1 having a 15 molded, transparent connective part 2. The connective part 2 includes a female socket 3. The inner end of the socket 3 is provided with a longitudinal bore 7 having a relatively small diameter. The bore 7 is provided with a contact surface 4 adjacent to which threads 5 for a set or lock screw are located in a bore 6 oriented orthogonally relative to the female socket. The housing is hermetically sealed also in relation to the molded part 2 and the contact between the interior electronics and the contact surface 4 is achieved by means of a feed-through. The feed-through is formed by a ceramic plug, typically made of alumina, into which one or more leads have been soldered. This lead is bonded (e.g. ultrasonically welded) to the electronics and to the contact surface 4. The ceramic plug is soldered or brazed by means of gold into a sleeve made of titanium. This operation may be made at any time before the assembly of the pacer housing. The sleeve is welded into an opening in the housing in a sealing manner during the assembly of the pacer housing that normally consists of two halves. Before the connective part is molded onto the housing, these halves are welded together and sealed.

Figure 2:
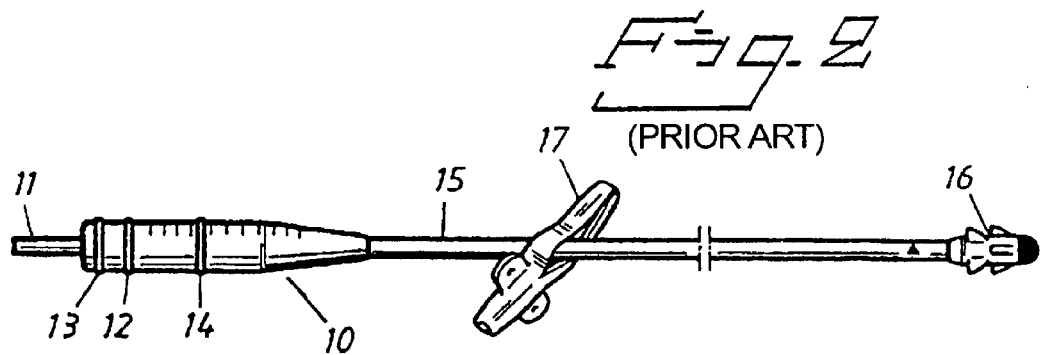
FIG. 2 shows a known lead with a male connective part.

FIG. 2 illustrates a lead 15 comprising a proximal connecting plug 10 and a distal, transvenous, intracardial electrode 16 as well as an attachment arrangement 17 for suturing the proximal end of the lead in the body of the patient. The connecting plug 10 is designed to be received in the socket 3 and the end thereof is provided with a longitudinally projecting contact pin 11 as well as a cylindrical body 17 provided with sealing rings 12, 13, 14 intended to engage and seal against the corresponding inner cylindrical surface of the female socket 3. The shape of the pin 11 corresponds to the shape of the bore 7. When the plug 10 is inserted into the socket 3 the pin 11 engages the contact surface 4 and the set-screw in the bore 6 can be tightened against the pin 11 in order to securely lock the plug 10 in the socket 3. The complexities involved in holding the bores, contact surfaces and threads in position and keeping them open and free from the molding material during the molding process are evident.

For simplicity, the above known device has 20 been illustrated as unipolar. A bipolar embodiment naturally will be more complex to manufacture. The preferred embodiments of the invention described below will relate to bipolar embodiments.

Figure 3:
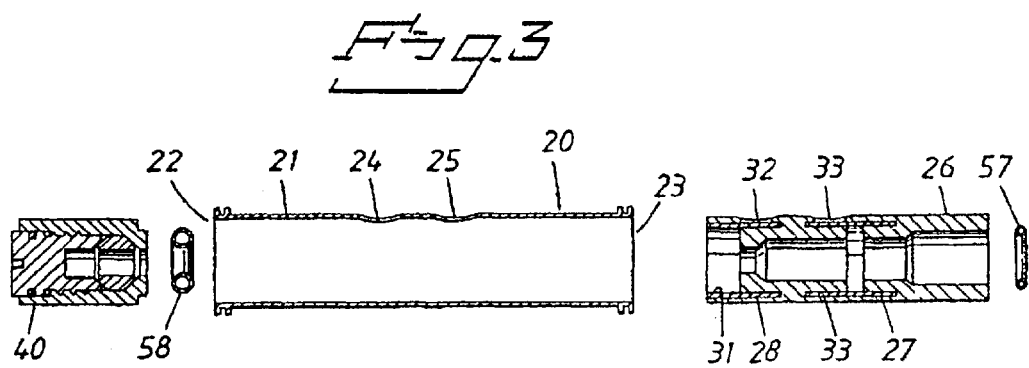
Figure 4:
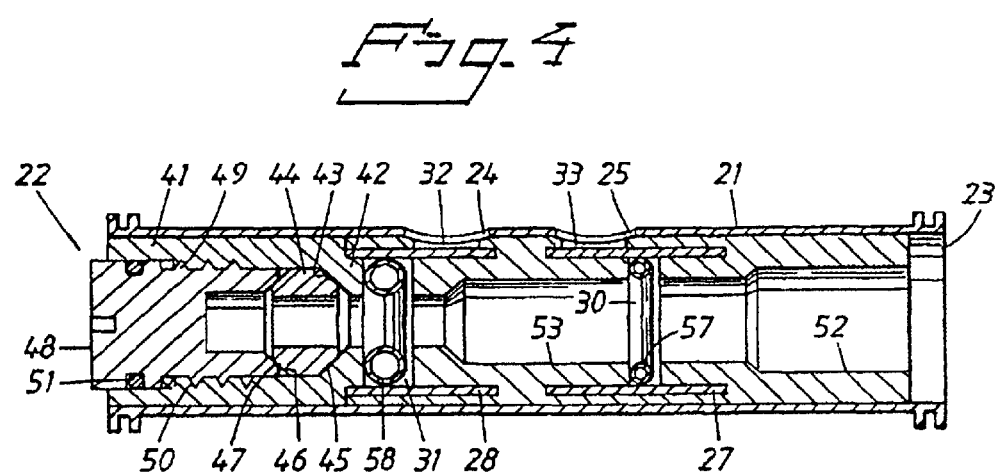
Figure 5:
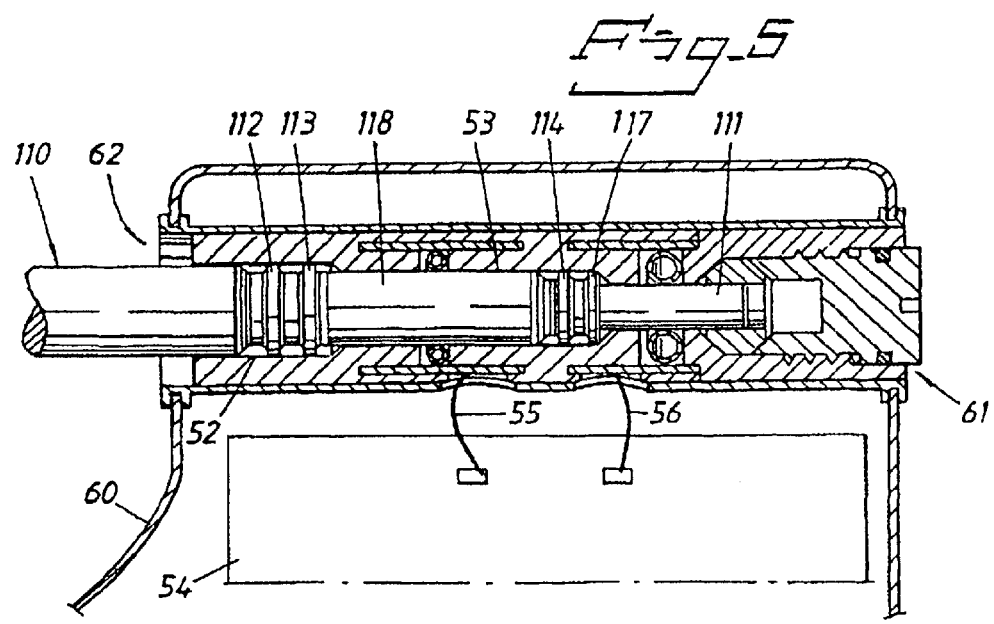

FIGS. 3–5 show a preferred embodiment of the invention comprising a tubular member 20. For clarity, the reference signs not repeated throughout all drawings.

The tubular member 20 is a tube 21 with two open ends 22, 23. Each end is to be welded into a respective opening in the pacer housing. The tube 21 is made of the same metal as the pacer housing, in this case titanium. The mid-section of the tube 21 is provided with two relatively small lateral openings 24, 25. The openings 24, 25 are sealed by means of a ceramic plug 26 fitting snugly in the tube 21 and soldered with gold against the inside of the tube 21. Two contact rings 27, 28 plug overlapping the lateral openings. The ceramic plug also originally could consist of several separate parts with the contact rings held between and soldered to these parts, thus uniting the parts of the plug to a unitary unit. The soldered junctions then would form an efficient seal.

It should be noted that the size of the openings 24, 25 which are necessary to allow the bonding of the leads to the parts of the contact rings accessible through the openings 24, 25 and 31, 32 is small, in relation to the entire circumference and to the length of the tube 21. The openings thus do not affect the structural integrity of the tube 21. The contact rings 27, 28, moreover, overlap the openings and are bonded thereto by means of the intermediate layer of ceramics, in this way strengthening the area in which said openings are located.

Typical dimensions for a tube intended to house a standard IS-1 male connector are for instance an inner diameter of 20 mm, a wall thickness of 0.3 mm (i.e. the same as the thickness of typical pacer housing walls) and a diameter of the holes 24, 25 of about 2 mm. A minimum area of about 4 $mm^2$ is necessary for the equipment presently used for bonding leads to metallic surfaces. The length of the tube 21 is of course adapted to the specific housing into which it is to be placed, but might typically be about 25 mm.

These dimensions of course can be varied as long as the tube remains structurally intact, i.e. as long as the tube has a strength and rigidity that is sufficient to prevent loads, including thermal stresses, on the housing and/or the connector to be transferred as tensile forces to the ceramic parts. Of course, low tensile forces not exceeding the tensile strength of the ceramic could be accepted. Since there are standards regarding the loads a pacer housing and connector should be able to withstand and regarding the dimensions only would involve standard stress calculations and dimensioning well within the scope of the man in the art. It should be noted that this also could take the degree of soldering between ceramic plug and tube into account, since this would determine the extent to which tube and ceramic would function as a composite without going outside the ordinary skill of the man skilled in the art.

The ceramic plug is provided with an interior bore 10 corresponding to the shape of the male connector in the same way as the molded prior art female connector described above and thus includes interior sealing surfaces 52, 53 for engagement with the sealing rings on the male connector.

A part 30, 31 of the inside of the contact rings is not covered with the ceramic material. In this way two inner circumferential grooves are obtained in the inner bore of the ceramic plug. The bottom of the grooves consists of the metal in the contact rings. Two openings 32, 33 are also provided in the outer surface of the ceramic plug that may be made to coincide with the lateral openings 24, 25 in the tube wall. These openings give access to the contact rings 27, 28 when the ceramic plug has been mounted correctly in the tube 21.

Thus, when the ceramic plug 26 has been soldered or bonded into place, the openings 24, 25 will be completely sealed by the plug 26 although allowing electrical connection to the interior of the tube 21 via the contact rings 27, 28.

To this extent the tubular member 20 can be manufactured in advance as desired.

Both ends of the prefabricated tube 21 can be welded to the pacer housing and the housing parts can be welded together after the connection of interior leads from the interior electronics to the contact rings 27, 28, should this be desired.

The remaining parts, i.e. the structures for achieving the contact between the contact rings and the contact surfaces on the male connector part on the lead, and for locking or fixating the male connector part in the socket, can easily be inserted afterwards. This means, for instance, that these parts would not interfere with the standard helium-based procedures for testing the housing with connector for leaks or that these parts would not be affected by the leak testing procedure.

FIG. 3 shows the main components of the tubular member 20, the tube 21 with openings 24, 25, the ceramic plug 26, a fixation part 40 and two circular spring contacts 57, 58. The spring contacts are similar to the spring contacts used in U.S. Pat. No. 4,934,366.

The fixation part 40, shown in more detail in FIG. 4, is designed in the same way as the lead locking device disclosed in U.S. Pat. No. 4,784,141, incorporated herein by reference, and has a hollow cylindrical part 41 fitting into the end of the tube 21. The inner end of the cylindrical part 41 is provided with an interior flange 42 with an inner conical surface 43. The locking device further comprises a resilient locking ring 44 located adjacent the flange 42. One side of the ring has a conical surface 45 that is complementary to the conical surface 43. The other side of the ring also has a conical surface 46 that is complementary to a conical surface 47 on a plug 48 provided with exterior threads 49 fitting into interior threads 50 on the inside of the cylindrical part 41. The outside of the plug 48 is provided with an O-ring 51 that is located in a peripheral groove 52 and sealingly engages the inside of the cylindrical part 41. When the plug 48 is screwed into the cylindrical part 41, the resilient ring 44 will be forced inwardly into contact with the contact pin of the male connector part by means of the interaction of the different conical surfaces, thus locking the contact pin inside the tube 21.

The tube 21 preferably is of the same material as the pacer housing, which normally is made of titanium. The ceramic plug may for instance be made of alumina, $Al_2O_3$, and the contact rings may for instance be made of stainless steel or of titanium.

In the above embodiment the ceramic plug has been illustrated as extending from the end of the tube and past the openings in the side of the tube. It is, however, only necessary that the ceramic plug cover the openings. The remaining part can be designed as a separate part inserted and bonded to the tube after the assembly of the pacer housing in a similar way as the fixation part 40.

FIG. 4 shows the tube 21 with all component parts mounted.

FIG. 5 shows how the tube 21 has been mounted in a pacer housing 60 and welded to openings 61, 62 in the openings via flanges located on the outside of the tube ends. FIG. 5 also shows a male connector plug 110 inserted in the tubular member. The plug has a contact pin 111, a contact surface 118 and four sealing rings 112, 113, 114, 117. The resilient ring 44 grips the pin 111 and the sealing rings 112–114, 117 are in engagement with the interior sealing surfaces 52, 53.

The connector can be achieved in a simple way compared 30 with the known molded connector means.

As mentioned above, the ceramic part can be soldered into the tube 21 in advance by similar methods as used when obtaining the feed-through in the prior art. The tube 21 then is placed in the openings in one of the pacer housing halves and conductors 55, 56 are bonded (typically by means of the electronic board 54 and to the parts of the contact rings that are accessible via the openings in the tube. The housing halves then are assembled and the two halves and the ends of the tube are welded together by means of a laser beam to form a sealed unit. This unit then is tested for leakage, for instance by means of standard helium-based procedures. It should be noted that no other kinds of work operations than those already used in the prior art are necessary.

The pacer then is finished by slipping the resilient spring contacts into the respective interior grooves in the ceramic plug and by inserting and bonding the lead locking mechanism into place in the corresponding open end of the tube.

The new connective part thus is very simple to manufacture and to mount in the pacer housing. The welding and sealing of the housing only includes the additional step of welding the ends of the tube to the edges of the openings in the housing, which is done in the same operation as the welding of the two housing halves. After the welding operation, no further operations are necessary, except for the simple insertion of contact rings and lead locking mechanism.

Since the tube after the welding operation in principle forms an integral, load-carrying part of the pacer housing, a high degree of tightness and integrity is obtained. The tube will ensure a high strength and a high durability of the connective part, whilst the ceramic plug will ensure a high degree of tightness in view of the large contact area between ceramic plug and tube that can used for soldering, i.e. sealing.

Although a pacer housing with one tubular member has been 35 illustrated, the housing of course can contain several members. The housing also wholly or partly could be made of openings holding the tube 21 are of metal or of a material allowing a bond of sufficient strength to the metal tube 21. Furthermore, although the tube 21 has been illustrated as having a circular cross-section, other cross-sections are possible.

An important advantage with the connector according to the invention is that the connecting pin 111 on the end of the lead can be reached from the outside through the end of the tube containing the lead locking mechanism. This will facilitate the removal of the male connector from the female socket since the pin 11 can be pushed outwardly through said second end by means of a tool if the male connector proves to be difficult to pull out. In the above, preferred embodiment it is sufficient to unscrew the threaded plug 48, thus exposing the end of the contact pin 111. Furthermore, in this state a stylet could be introduced into the longitudinal channel, for instance for repositioning the electrode with the aid of the internal electronics in the pacer. The plug 48 could also contain a sealable, longitudinal bore, for instance sealed by a screw, for this purpose.

Another important feature of the invention is the possibility of achieving a high capacitance between contact ring and tube by allowing the ceramic plug and one of the contact rings to extend all the way to one end of the tube. The ring and the tube will be separated by the ceramic, which is chosen to be insulating and thus is a dielectric. Connecting a small capacitor between the ring and the tube can increase the capacitance further.

Another important advantage of a high capacitance is that it helps avoid interference.

Although modifications and changes may be suggested by those skilled in the art, it is the intention of the inventors to embody within the patent warranted hereon all changes and modifications as reasonably and properly come within the scope of their contribution to the art.

We claim:

1. A pacemaker comprising:

a metallic housing having a first wall with a first opening therein and a second wall with a second opening therein;

a metallic tubular member having a first tube end disposed in and attached to said first opening and an opposite second tube end disposed in and attached to said second opening, said tubular member being substantially continuous between said first tube end and said second tube end; and a plurality of interior components disposed within said tubular member adapted to make electrical contact with contact surfaces of a contact plug adapted for insertion into said tubular member.

2. A pacemaker as claimed in claim 1 wherein said first and second tube ends are respectively bonded to said metallic housing at said first and second openings.

3. A pacemaker as claimed in claim 1 wherein said first and second tube ends are respectively welded to said metallic housing at said first and second openings.

4. A pacemaker as claimed in claim 1 wherein said metallic tubular member has at least one lateral opening therein, and having a contact surface disposed in said lateral opening for establishing electrical contact between the interior of said metallic tubular member and an exterior of said metallic tubular member, said contact surface being electrically connected to at least one of said interior components.

5. A pacemaker as claimed in claim 4 further comprising an insulating ceramic plug disposed in and closing said lateral opening, said ceramic plug being mechanically attached in said lateral opening and holding said contact surface in said opening.

6. A pacemaker as claimed in claim 5 wherein said ceramic plug is soldered in said lateral opening.

7. A pacemaker as claimed in claim 5 wherein said ceramic plug is bonded in said lateral opening.

8. A pacemaker as claimed in claim 5 wherein said contact surface is a metallic ring and wherein said ceramic plug has an exterior with a lateral opening therein in registry with said lateral opening in said metallic tubular member allowing access to said ring from said exterior of said metallic tubular member.

9. A pacemaker as claimed in claim 8 wherein said metal ring has a central portion which is free of ceramic of said ceramic plug, producing a peripheral groove at an interior of said ring allowing access to said ring from said interior of said metallic tubular member.

10. A pacemaker as claimed in claim 1 further comprising a locking arrangement disposed at said second tube end, and accessible from said second tube end, adapted for locking an end of an electrode lead in said metallic tubular member.

11. A pacemaker as claimed in claim 10 wherein said locking arrangement is at least partially removable from said metallic tubular member to allow access to said end of said electrode lead.

\* \* \* \* \*